United States Patent [19]

Regnat et al.

[11] Patent Number: 5,739,372

[45] Date of Patent: Apr. 14, 1998

[54] OXAPHOSPHORINS AND A PROCESS FOR THEIR PREPARATION

[75] Inventors: Dieter Regnat, Eppstein; Hans-Jerg Kleiner, Kronberg, both of Germany

[73] Assignee: Hoechst Aktiengesellschaft, Frankfurt AM Main, Germany

[21] Appl. No.: 659,897

[22] Filed: Jun. 7, 1996

[30] Foreign Application Priority Data

Jun. 12, 1995 [DE] Germany ............... 195 21 339.4

[51] Int. Cl.$^6$ ...................................... C07F 9/6574
[52] U.S. Cl. .................................. 558/82; 549/200
[58] Field of Search ............................................. 558/82

[56] References Cited

U.S. PATENT DOCUMENTS 3,702,278  11/1972  Saito et al. ........................ 260/936
5,391,798   2/1995  Kleiner ................................ 558/82

FOREIGN PATENT DOCUMENTS 0582957  2/1994  European Pat. Off. .
2034887  1/1972  Germany .

*Primary Examiner*—Mukund J. Shah
*Assistant Examiner*—Pavanaram K. Sripada
*Attorney, Agent, or Firm*—Connolly & Hutz

[57] ABSTRACT

The present invention relates to oxaphosphorins of the formula

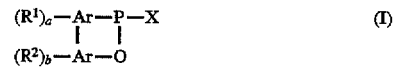

where Ar-Ar is 1-phenylnaphthyl or 1,1'-binaphthyl, $R^1$ and $R^2$ are identical or different and are F, Cl, alkyl or alkoxy each having from 1 to 8 carbon atoms or substituted or unsubstituted aryl, a and b are identical or different and are each an integer from 0 to 4, or Ar-Ar is biphenyl, $R^1$ and $R^2$ are identical or different and are substituted or unsubstituted aryl, a and b are as defined above, but a+b≧1, X is Cl or Br and the Ar-P and Ar-O bonds are each arranged in the ortho position to the Ar-Ar bond.

The invention further relates to a process for preparing these oxaphosphorins.

14 Claims, No Drawings

OXAPHOSPHORINS AND A PROCESS FOR THEIR PREPARATION

Oxaphosphorins are known in the form of 6-chloro(6H)-dibenz-[c,e][1,2]-oxaphosphorins, whose preparation is described in detail in DE-A 2 034 887 and EP-A-0 582 957.

6-Chloro(6H)-dibenz-[c,e][1,2]-oxaphosphorin is an industrially important intermediate for preparing flame retardants (DE-C 26 46 218; DE-C 27 30 371), additives in polymerization processes (EP-A-0 454 462), photo-initiators, stabilizers for polymers and photographic material. This wide range of opportunities for making industrial use of the oxaphosphorin system, which is interesting because of its reactivity, is however restricted by the fact that oxaphosphorins are available exclusively in the form of the dibenzoxaphosphorins.

In view of the opportunities which the oxaphosphorin system opens up for a large number of chemical syntheses, it is a rewarding object to provide new compounds from this group of substances. This not only increases the range of possible applications, but also allows the material properties and structural features of the oxaphosphorins to be varied. It may be assumed that the chemical nature and the structure of the new oxaphosphorins can be advantageously utilized to prepare further, possibly phosphorus-containing, organic compounds, with the chemical nature and the structure being transmitted completely or partially to the compounds to be prepared.

This object is achieved by oxaphosphorins of the formula

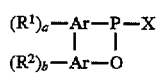

(I)

where Ar-Ar is 1-phenylnaphthyl or 1,1'-binaphthyl, $R^1$ and $R^2$ are identical or different and are F, Cl, alkyl or alkoxy each having from 1 to 8 carbon atoms or substituted or unsubstituted aryl, a and b are identical or different and are each an integer from 0 to 4, or Ar-Ar is biphenyl, $R^1$ and $R^2$ are identical or different and are substituted or unsubstituted aryl, a and b are as defined above, but a+b≧1, X is Cl or Br and the Ar-P and Ar-O bonds are each arranged in the ortho position to the Ar-Ar bond.

The oxaphosphorins of the invention are interesting compounds since they have a chiral P atom and additionally contain, in the cases where Ar-Ar is 1-phenylnaphthyl or 1,1'-binaphthyl, a chiral organic radical. The oxaphosphorins in which Ar-Ar is biphenyl likewise have a chiral P atom and the biphenyl radical, if it is not symmetrically substituted, gives the oxaphosphorin molecule additional asymmetry.

They are of particular importance for the preparation of further substances, with the chirality of the P atom and possibly the chirality or asymmetry of the organic radical being utilized for the synthesis. As described in the German Patent Application (number 19 521 340.8) filed on the same day as the present patent application, the oxaphosphorins are advantageous as starting materials for the preparation of hydroxybiarylphosphines.

In particular, the present invention provides oxaphosphorins of the formula (I) in which Ar-Ar is 1-phenylnaphthyl or 1,1'-binaphthyl, $R^1$ and $R^2$ are identical or different and are F, Cl, alkyl or alkoxy each having from 1 to 4 carbon atoms or phenyl, a and b are identical or different and are 0 or 1, or Ar-Ar is biphenyl, $R^1$ and $R^2$ are identical or different and are substituted or unsubstituted phenyl and a+b is 1 or 2.

Of particular importance are oxaphosphorins of the formula (I) in which Ar-Ar is 1-phenylnaphthyl or 1,1'-binaphthyl and a and b are 0, or Ar-Ar is biphenyl, $R^1$ or $R^2$ is phenyl and a+b=1. These oxaphosphorins are comparatively readily accessible since they can be prepared without a great outlay using starting materials which are relatively easy to obtain.

The invention provides particularly the following oxaphosphorins of the formulae (II), (III), (IV) and (V), namely

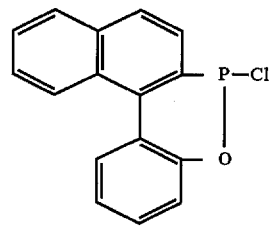

(II)

6-chloro-6H-benzo[e]naphth[2,1-c][1,2]oxaphosphorin

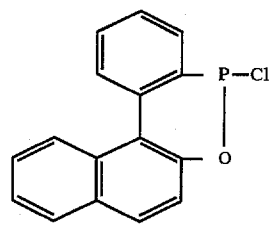

(III)

5-chloro-5H-benzo[c]naphth[1,2-c][1,2]oxaphosphorin

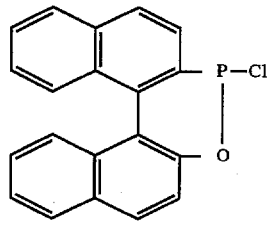

(IV)

3'-chloro-3H-dinaphth[2,1-c:1',2'-e][1,2]oxaphosphorin and

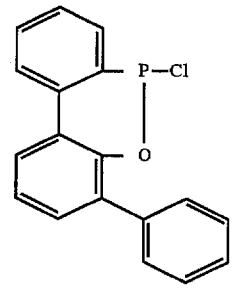

(V)

6-chloro-6H-4-phenyldibenz[c,e][1,2]oxaphosphorin.

It is also an object to develop a synthetic route which enables the abovementioned oxaphosphorins to be obtained in a simple manner without a great outlay and which can also be easily implemented in industry.

This object is achieved by a process for preparing the abovementioned oxaphosphorins. It comprises reacting a compound of the formula

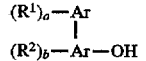

(VI)

where $R^1$, $R^2$, a, b, Ar-Ar are as defined above and the OH group is arranged in the ortho position to the Ar-Ar bond, with PX$_3$, where X is Cl or Br, and a Lewis acid as catalyst at from 140° to 300° C. with elimination of hydrogen halide.

The order in which the phosphorus trihalide PX$_3$ and the Lewis acid are added is generally not subject to any conditions. In one process variant, the compound of the formula (VI) can be admixed with the Lewis acid, heated to the prescribed reaction temperature and PX$_3$ can subsequently be added.

However, according to another process variant, it is possible to admix the compound of the formula (VI) with PX$_3$, heat the mixture to the prescribed reaction temperature and subsequently add the Lewis acid.

The compound of the formula (VI) and PX$_3$ are used in a stoichiometric ratio or PX$_3$ is used in excess. The compound of the formula (VI) and PX$_3$ are usually used in a molar ratio of from 1:1 to 1:1.5, in particular from 1:1.1 to 1:1.3. Excess PX$_3$ used is removed by distillation after the reaction is concluded.

As catalyst, use is made of the Lewis acids customarily used, for example halides, in particular chlorides, of the elements of groups IIb and IIIa of the Periodic Table of the Elements.

A well suited Lewis acid is zinc chloride.

The Lewis acid is usually used in an amount of from 0.05 to 20% by weight, in particular from 0.5 to 10% by weight based on the compound of the formula (VI).

In a number of cases it has been found to be sufficient to carry out the reaction at from 160° to 270° C., in particular from 190° to 250° C.

The reaction can be allowed to proceed at subatmospheric pressure, atmospheric pressure or superatmospheric pressure, taking note of the fact that the hydrogen halide eliminated is to be removed from the reaction mixture. The crude mixture formed can, if desired or required, be further purified by customary methods, for example by distillation and/or crystallization.

The following examples illustrate the invention without restricting it thereto.

Experimental part

EXAMPLE 1

Preparation of 6-chloro-6H-benzo[e]naphth[2,1-c][1,2]-oxaphosphorin 60 g (0.273 mol) of o-naphthylphenol and 0.6 g of zinc chloride are heated to 200° C. while stirring. 46 g (0.335 mol) of phosphorus trichloride are then added dropwise over a period of 5 hours and the mixture is subsequently stirred further for 4 hours under reflux. The off-gas (HCl) eliminated is conducted away. The mixture is then cooled and the excess phosphorus trichloride is distilled off under reduced pressure. The residue is distilled at a bath temperature of from 200° to 225° C. and 0.2 mbar by means of a bulb tube. This gives 51 g of 6-chloro-6H-benzo[e]naphth[2,1-c][1,21] oxaphosphorin which solidify in crystalline form. This corresponds to a yield of 66% of theory.

| $C_{16}H_{10}ClOP$ | calc.: | 67.48% C | 3.52% H | 10.9% P |
|---|---|---|---|---|
| (284.5) | found: | 67.5% C | 3.45% H | 10.8% P |

EXAMPLE 2

Preparation of 5-chloro-5H-benzo[c]naphth[1,2-e][1,2]-oxaphosphorin 10.9 g (0.0496 mol) of o-phenylnaphth-2-ol and 0.3 g of zinc chloride are heated to 200° C. under a nitrogen atmosphere and 8.3 g (0.06 mol) of phosphorus trichloride are slowly added dropwise while stirring. When off-gas (HCl) can no longer be observed, the mixture is boiled under reflux for a further 30 minutes. It is then cooled and the excess phosphorus trichloride is distilled off under reduced pressure. The residue is distilled at a bath temperature of from 175° to 200° C. and 0.2 mbar by means of a bulb tube. This gives 12 g of 5-chloro-5H-benzo[c]naphth[1,2-e][1,2] oxaphosphorin which solidify in crystalline form (melting point: 123°–126° C.).

This corresponds to a yield of 85% of theory.

| $C_{16}H_{10}ClOP$ | calc.: | 67.48% C | 3.52% H | 10.9% P |
|---|---|---|---|---|
| (284.5) | found: | 67.4% C | 3.5% H | 10.4% P |

EXAMPLE 3

Preparation of 3-chloro-3H-dinaphth[2,1-c:1',2'-e][1,2]-oxaphosphorin 20 g (0.146 mol) of phosphorus trichloride are heated to 75° C. under a nitrogen atmosphere and 31.5 g (0.117 mol) of o-naphthylnaphth-2-ol are introduced in portions while stirring. The mixture is then slowly heated to 150° C. with evolution of hydrogen chloride. It is then cooled and 0.3 g of zinc chloride is added. The mixture is subsequently slowly heated until a temperature of 245° C. is reached. The reaction mixture remains at this temperature until evolution of hydrogen chloride can no longer be observed. After cooling, the excess phosphorus trichloride is distilled off. The residue contains 40% of the end product ($^{31}$P-NMR (CDCl$_3$) δ=131.94 ppm) which can be obtained in pure form by column chromatography.

| $C_{20}H_{12}ClOP$ | calc.: | 71.74% C | 3.59% H | 9.27% P |
|---|---|---|---|---|
| (334.5) | found: | 71.5% C | 3.5% H | 9.1% P |

EXAMPLE 4

Preparation of 6-chloro-(6H)-4-phenyldibenz[c,e][1,2]-oxaphosphorin 25 g (0.102 mol) of 2,6-diphenylphenol and 0.27 g of zinc chloride are heated while stirring to 200° C. under a nitrogen atmosphere. 17.4 g (0.127 mol) of phosphorus trichloride are then added dropwise over a period of one hour and after a total of 90 minutes another 2 g of phosphorus trichloride are added dropwise and the mixture is maintained at 200° C. under reflux. The off-gas (HCl) eliminated is conducted away. After a total of two hours, the mixture is cooled and the excess phosphorus trichloride is distilled off under reduced pressure. The residue is subsequently distilled at 0.1 mbar, with the product going over at 188° C. This gives 29 g, corresponding to a yield of 92% of theory.

| $C_{18}H_{12}ClOP$ | calc.: | 69.57% C | 3.87% H | 9.98% P |
|---|---|---|---|---|
| (310.5) | found: | 69.3% C | 3.91% H | 9.8% P |

We claim:

1. An oxaphosphorin of the formula

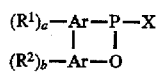  (I)

where Ar-Ar is 1-phenylnaphtyl or 1,1'-binapthyl, $R^1$ and $R^2$ are identical or different and are F, Cl, alkyl or alkoxy each having from 1 to 8 carbon atoms or substituted or unsubstituted aryl, a and b are identical or different and are each an integer from 0 to 4, X is Cl or Br and the Ar-P and Ar-O bonds are each arranged in the ortho position to the Ar-Ar bond.

2. An oxaphosphorin as claimed in claim 1, wherein Ar-Ar is 1-phenylnaphtyl or 1,1'-binaphthyl, $R^1$ and $R^2$ are identical or different and are F, Cl, alkyl or alkoxy each having from 1 to 4 carbon atoms or phenyl, a and b are identical or different and are 0 or 1.

3. An oxaphosphorin as claimed in claim 1, wherein Ar-Ar is 1-phenylnaphtyl or 1,1'-binaphtyl and a and b are 0.

4. An oxaphosphorin as claimed in claim 1, corresponding to the formula

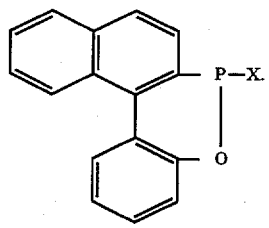  (II)

5. An oxaphosphorin as claimed in claim 1, corresponding to the formula

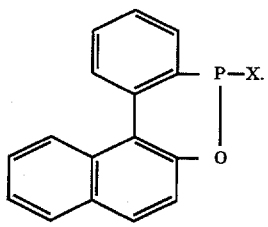  (III)

6. An oxaphosphorin as claimed in claim 1, corresponding to the formula

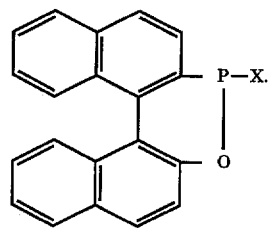  (IV)

7. A process for preparing the oxaphosphorins as claimed in claim 1, which comprises reacting a compound of the formula

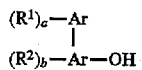  (VI)

where $R^1$, $R^2$, a, b, Ar-Ar are as defined above and the OH group is arranged in the ortho position to the Ar-Ar bond, with $PX_3$, where X is Cl or Br, and a Lewis acid as catalyst at from 140° to 300° C. with elimination of hydrogen halide.

8. The process as claimed in claim 7, wherein the compound of the formula (VI) is admixed with the Lewis acid, heated to the prescribed reaction temperature and $PX_3$ is added.

9. The process as claimed in claim 7, wherein the compound of the formula (VI) is admixed with $PX_3$, heated to the prescribed reaction temperature and the Lewis acid is added.

10. The process as claimed in claim 7,
   wherein the compound of the formula (VI) and $PX_3$ are used in a molar ratio of from 1:1 to 1:1.5, in particular from 1:1.1 to 1:1.3.

11. The process as claimed in claim 7,
   wherein the Lewis acid used is a halide of an element of groups IIb and IIIa of the Periodic Table of the Elements.

12. The process as claimed in claim 7,
   wherein the Lewis acid used is zinc chloride.

13. The process as claimed in claim 7,
   wherein the Lewis acid is used in an amount of from 0.05 to 20% by weight, in particular from 0.5 to 10% by weight, based on the compound of the formula (VI).

14. The process as claimed in claim 7,
   wherein the reaction is carried out at from to 270° C., in particular from 190° to 250° C.

* * * * *